United States Patent [19]

Eichler

[11] 4,245,628
[45] Jan. 20, 1981

[54] BACK SUPPORT DEVICE

[76] Inventor: Joachim Eichler, Mosbacher Strasse 10, 6200 Wiesbaden, Fed. Rep. of Germany

[21] Appl. No.: 68,612

[22] Filed: Aug. 22, 1979

[30] Foreign Application Priority Data

Aug. 29, 1978 [DE] Fed. Rep. of Germany ....... 2837620

[51] Int. Cl.³ .............................................. A61F 5/02
[52] U.S. Cl. ..................................................... 128/78
[58] Field of Search ............... 128/69, 78, 95.96, 567, 128/518 R, 538, 573, 520, 522, 562, 563

[56] References Cited

U.S. PATENT DOCUMENTS

| 3,068,860 | 12/1962 | Strandas | 128/78 |
| 3,561,434 | 2/1971 | Kilbey | 128/78 X |
| 3,717,143 | 2/1973 | Johnson | 128/78 |
| 3,927,665 | 12/1975 | Wax | 128/78 |
| 4,135,503 | 1/1979 | Romano | 128/78 |

Primary Examiner—Stephen C. Pellegrino

[57] ABSTRACT

A back support device of variable pressure action by means of which a directed segmental treatment can be carried out and atrophy of the back extensors avoided.

10 Claims, 4 Drawing Figures

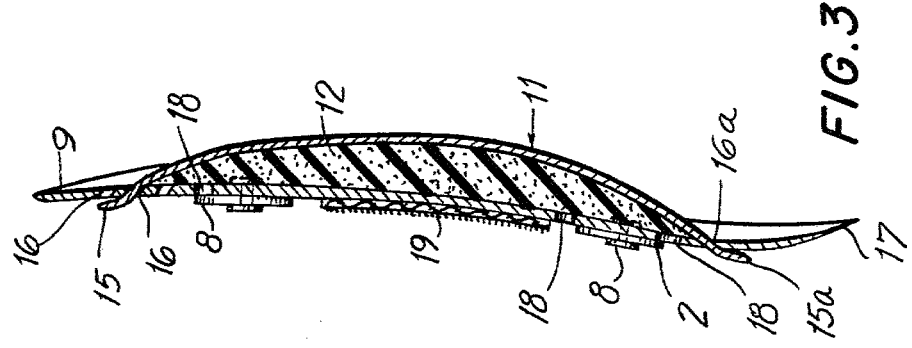
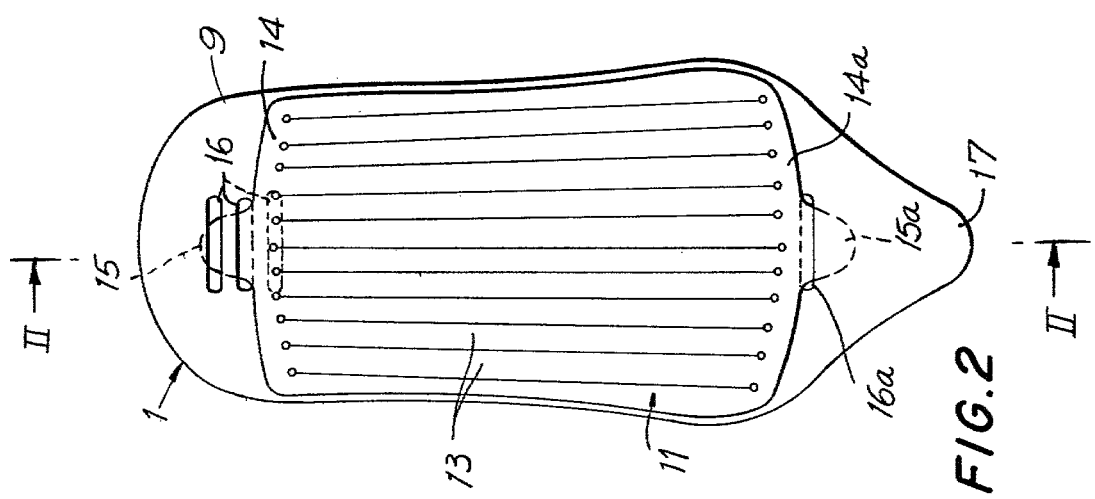

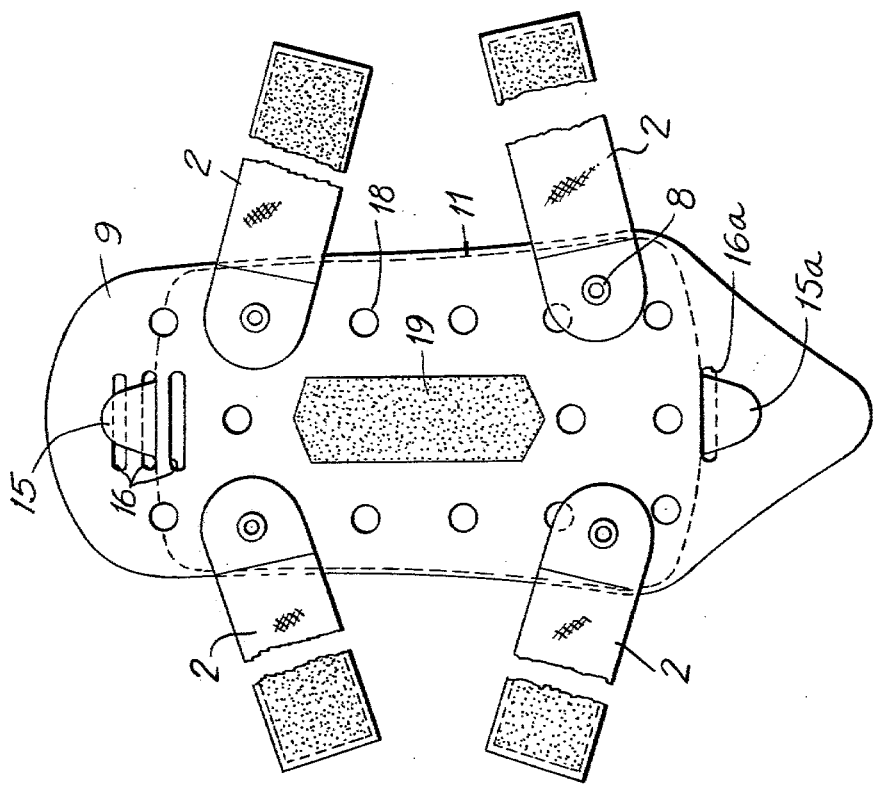

BACK SUPPORT DEVICE

This invention relates to a back support device, more particularly, to a device which supports the human spinal column.

BACKGROUND FOR THE INVENTION

Orthopedic bandages and corsets have been used for a long time for treating certain back ailments. Corsets of metal are used in cases of pronounced scoliosis (curvature of the spine with formation of a hump) or inflammatory ailments of the vertebrae and intervertebral disks (for instance, tuberculosis of the vertebrae). Chronic pain in the lumbar vertebral column and the sacral region are treated with spinal column support bandages, support braces or support clamps.

It is known to provide back support bandages with a rigid support pad which permits a certain supporting of the lower lumbar vertebral column and of the abdomen. Rigid pads, however, have the disadvantage that these can result in atrophy of the extensors of the back by maintaining them immovable.

GENERAL DESCRIPTION OF THE INVENTION

The object of the present invention is to provide a back support device, i.e., a composite bandage, of variable pressure action by means of which a directed segmental treatment can be carried out and atrophy of the back extensors be avoided.

The back support bandage with support pad fastened thereto in accordance with the invention comprises the support pad consisting of a substantially rigid fastening plate attached to the support bandage, a rib plate which is arched away from the fastening plate (and towards the spinal column) and fastened at its upper and lower ends to the fastening plate and a foam cushion which takes up the space between the fastening plate and the rib plate, the rib plate having flexible ribs which are separated from each other and arranged parallel to each other. These ribs consist of a resilient material and extend between the two fastened ends of the rib plate and are fastened in the vicinity of the rib plate ends. The rib plate as such and/or the individual ribs thereof may consist of metal or plastic, insofar as this material possesses elastic resiliency. Thus, for instance, the ribs may consist of flexible, resilient sheet metal and be attached, e.g., riveted or soldered, to a plastic or metal frame forming the rib plate, but it is advisable to make the rib plate integral with the individual ribs from a single material, such as a steel sheet or a plastic. The latter is preferred because of its lighter weight. With such a one-piece development of the rib plate, the plate is divided into parallel slots in longitudinal direction between the two fastening ends, which slots however terminate in each case in front of the fastening end of the rib plate so that a web which is approximately perpendicular to the ribs is formed in the two fastening ends, to which web the individual ribs are connected integrally.

The rib plate can be firmly connected to the fastening plate at the two fastening ends of the rib plate. However, it is preferably detachably connected to it. It is particularly advisable to effect the attachment by means of two insertable straps (i.e., tongues) at the two ends of the rib plate, which straps are advisedly arranged in the central region of the fastening ends of the rib plate. According to this arrangement, the rib plate can yield laterally by different degrees. The fastening of a rib plate by straps to the two fastening ends is effected by inserting said straps into slots in the fastening plate which are arranged substantially perpendicularly to the lengthwise direction of the ribs.

It is particularly suitable to be able to change the pressure on the human back of the rib plate. For this purpose, it is advisable to provide a plurality of slots extending parallel to each other on the fastening plate in the region of at least one of the fastening ends of the rib plate so that the strap on said fastening end of the rib plate can be extended into any one of these parallel slots. Depending on the slot into which the strap of the rib plate is placed, the rib plate is arched to a greater or lesser extent towards the spinal column. The strongest arching is obtained when the strap is inserted into the slot which is closest to the first or sole slot at the other fastening end of the rib plate. The arching of the rib plate is somewhat greater in the lower region, i.e., in the direction towards the coccyx, than in the upper region and may be accomplished by the designing of a proper curvature of the fastening plate and/or varying the thickness of the rib(s) as further explained below.

The fastening plate consists of a substantially rigid material, such as, for instance, metal or plastic. The shape of the fastening plate is advisedly such that it follows the sagittal curved course of a lumbar vertebral column up to the coccyx, without consideration of the lumbar lordosis, and tapers at the lower end, which is advisedly bent towards the rib plate. This tapering is furthermore arched somewhat towards the side of the rib plate.

This fastening plate serves, on the one hand, to hold the arching of the rib plate taut and, on the other hand, to fasten the entire support pad to the support bandage. This attachment is advisedly effected by means of straps and/or by means of a "Velcro" (TM) connection which is fastened on the one hand on the rear side of the fastening plate which faces away from the foam cushion and on the other hand to the inner side of the support bandage which carries an opposite "Velcro" (TM) connection. The fastening straps for surrounding the human body are advisedly applied to the fastening plate by means of hollow rivets so that the fastening in itself is movable. The fastening plate can be subdivided in its height, advisedly into two or three parts, which are connected with each other by joints so that the fastening plate does not protrude upon a wearer's bending forwardly.

The fastening plate advisedly has air holes in order to avoid excessive sweating of the wearer in the region of the pad. Since the rib plate is also interrupted by the formation of the ribs and the foam present between same may be pervious to water vapor and air, the entire pad can be made so pervious that undesired sweating is avoided. The fastening plate can also be provided in its center with a cutout, about 3.5 cm in width and about 16 cm in length, in order to relieve the spinous processes from stress.

The foam cushion between the fastening plate and the rib plate must have sufficient elasticity and strength to move away under load upon a change in the hollow space between the fastening plate and the rib plate by different arching of the rib plate and by the impressing of individual ribs and always substantially completely fill out the hollow space. For this purpose, known foam plastics can be used.

The support bandage to which the fastening plate and rib plate is attached may be of various kinds and be of traditional shape and structure. However, it is advisable that the fastening plate be fastened on each side to (in each case) one strap (which is connected at two points to the fastening plate and which passes through two slots through the support bandage to the outside thereof). The strap(s) extends and is anchored to a ring part to which there is additionally fastened an individual fastening strap, such as, by way of example in the drawing. In this way, the fastening of the support pad to the support bandage is movable in itself and does not result in any undesired stresses.

The above-described development of the fastening plate which corresponds to the sagittal curved course of a lumbar vertebral column up to the coccyx, without consideration of the lumbar lordosis, has at its lower end an opposite curvature for the sacrum and coccyx. The rib plate, due to the arching, has a stronger curvature, which corresponds to the normal transition from the lumbar vertebral column to the coccyx. The foam cushion between the rib plate and the fastening plate serves to distribute uniformly the pressure exerted by the ribs of the rib plate.

In certain cases, it may be advisable to omit a few ribs in the rib plate, for instance two to four ribs in the central section, or to make them weaker (by making them thinner at appropriate places) and in this way, avoid pressure on the spinous processes. Instead of this, or together with it, some of the outer ribs, such as, for instance, once again, two to four, can be thickened, as for instance by the pasting thereon of webs of the same size which increases the massaging action of the outer webs in the region of the back entensors. In this variant also, the pressure action on the spinous processes is less. The rib plate can also be made of plastic of different thickness so that it can be used optionally for delicate women, for standard patients, or for athletes.

The action of the back support bandage of the invention is as follows. The pressure action on the back extensors differs. Depending on the inclination of the pelvis and the bending or over-stretching of the lumbar vertebral column, given segemental muscle sections are placed under pressure and thus massaged. When sitting on a chair, this action can be further increased on the right or on the left side by pressing against the back of a chair at a given height. By loosening or tightening the rib plate straps, i.e., changing the rib plate arch, a weakening or strengthening of the massaging action is also possible.

The back support bandage of the invention induces the patient, without his knowledge, to maintain a constant positive correction of posture. The back support bandage is namely least felt when a healthy posture is assumed.

Since the pressure and thus the massaging action occur only over a length of a few centimeters, a directed segmental self-treatment can be carried out. By the difference in the pressure action, atrophy of the back extensors such as would take place with rigid pads is avoided. Due to the active movements which the patient must carry out with his spinal column in order to relax his muscles, a certain strengthening of the back extensors can even take place.

The flexibility of the rib plate also prevents the pad from slipping. Only in extreme cases need the back support bandage be provided with a suspender strap. The rib plate, furthermore, also has a certain heating effect which improves the circulation of the back extensors in the lumbar region. The slots between the individual ribs, however, as already mentioned, prevent excessive formation of perspiration.

The back support bandage of the invention can be used in the case of chronic therapy-resistant pain syndromes (lumbalgiae, lumbosciatica, lumbar syndrome) on the lumbar vertebral column which are caused by spondylarthrosis, spondylosis, lubosacral transition pains, hypermobility, spondylolysis, spondylolisthesis of the first degree, static complaints and myostatic insufficiency. Furthermore, the back support bandage of the invention is suitable for additional treatment after disk operations in order to shorten the postoperative phase of treatment. It can also be prescribed as additional treatment for fractured vertebrae after completion of the immobilizing phase.

DESCRIPTION OF THE INVENTION BY REFERENCE TO THE DRAWINGS

One embodiment of the invention is shown in the drawing wherein:

FIG. 2 is a plan rear view of the support pad as seen from the inside of the support bandage shown in FIG. 1 as 1 and fastened in the support bandage in that Figure;

FIG. 3 is a vertical section through the support pad along the line II—II in FIG. 2; and FIG. 4 shows the support pad with straps fastened thereto, seen from the obverse side to that shown in FIG. 2 and in front view of the support bandage as shown in FIG. 1.

Figure 1:
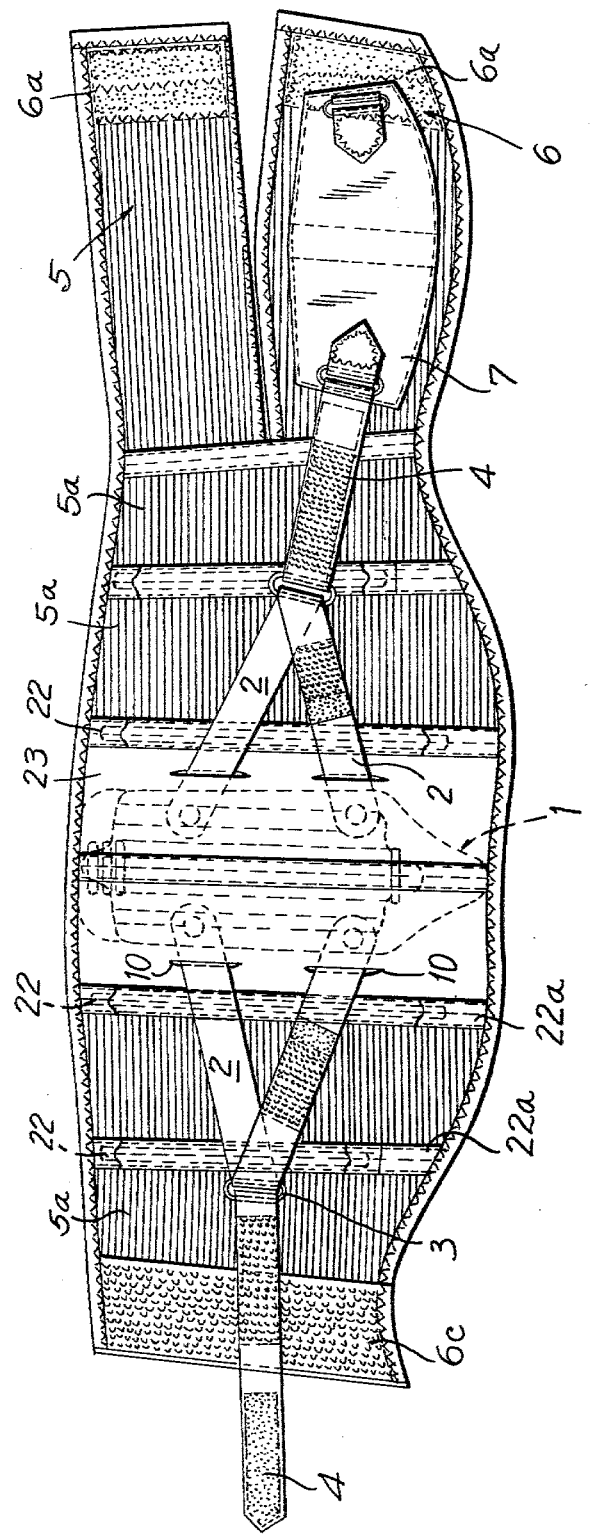
FIG. 1 is a plan front view of the entire support bandage, and shows a back support bandage in accordance with the invention as seen from the outside.

FIG. 1 shows the plan front view of the back support bandage of the invention as seen from the outside, the support pad which is fastened on the opposite side being designated generally by the reference number 1. As is more clearly shown in FIG. 4, straps 2 are fastened to the fastening plate 9 of the support pad 1 by means of hollow rivets 8 (shown in FIG. 4). These straps 2 extend through slots 10 in the support bandage to the outside thereof and pass there with a V-shaped course (or as individual straps forming a V) through an elongated ring part 3 to which another individual strap 4 is fastened. The support bandage furthermore is provided with tabs 5 and 6 for closing on the abdominal side of the patient, the tab 6 being provided with a fabric or plastic reinforcement 7 in the region of the abdomen. Furthermore, the support bandage has, in customary manner, various "Velcro" (TM) fasteners, which are well known and are shown in FIG. 1 as 6a and 6c, for the respective parts thereof. The straps 2, which have as a whole a V-shaped course, have been shown interrupted in the drawing and connected by "Velcro" (TM) type fasteners. In other respects, i.e., the webing shown in FIG. 1 as 5a is that conventional employed in the art, e.g., nylon, cotton, Spandex, Lycra, or various mixtures thereof. Similarly, support battens (sometimes called bones) 22 are sheathed in pockets 22a at appropriately spaced intervals, again, as it is well known in the art. Webbing 23 in which the support plate is incorporated is that conventionally used in this art, e.g., the same as for webbing 5a.

FIGS. 2 to 4 show the development of the support pad 1. It consists of the fastening plate 9, the arched rib plate 11, and the intermediate foam cushion 12.

The rib plate 11 consists of individual ribs 13 arranged parallel to each other and separated from each other by slots in the rib plate and is made, integral with the ribs, from a resilient material. The ribs 13 terminate at the two fastening ends of the rib plate 11 in a web 14 and 14a respectively. To each of these webs there is integrally fastened tabs 15 or 15a, respectively, and these tabs are pushed through slots 16 and 16a, respectively, in the fastening plate 9.

As its upper end, the fastening plate has a plurality of slots 16 arranged parallel to each other through which the tabs 15 can be passed in order to change the curvature of the rib plate 11.

The lower end 17 of the fastening plate 9 is tapered and curved inwardly.

The straps 2 are fastened by hollow rivets 8 to the fastening plate 9 as shown in FIG. 4. Furthermore, the fastening plate has air holes 18 and, in its center, a "Velcro" attachment 19 for further fastening to the support bandage webbing 23.

Numerous modifications of the embodiment shown can be effected without going beyond the scope of the invention.

What is claimed is:

1. A back support device comprising a bandage including a support pad of a substantially rigid fastening plate and a support bandage therefor, a rib plate secured at a lower and an upper end to said fastening plate arcuately from said fastening plate, a foam cushion between said fastening plate and said rib plate, said rib plate comprised of a plurality of flexible ribs substantially parallel to each other and independently flexible from each other, said ribs consisting of a resilient material and extending between an upper and a lower end of said rib plates and an upper and lower region of said fastening plate, and means for securement for said rib plate at said upper and lower regions thereof to said fastening plate.

2. A back support device as defined in claim 1, and wherein said flexible ribs are integral with said rib plate and of the same material as said rib plate.

3. A back support device as defined in claim 1, and wherein said rib plate is detachably secured to said fastening plate.

4. A back support device as defined in claim 1, and wherein said rib plate arcuately, adjustably extends from said fastening plate.

5. A back support device as defined in claim 4, wherein said rib plate at an upper and lower end thereof comprises a tongue for each end insertable into a slot in said fastening plate at a corresponding region thereof.

6. A back support device as defined in claim 1, wherein said fastening plate is fastened by a plurality of attachments to said support bandage.

7. A back support device as defined in claim 6, wherein said fastening plate has on each of its left and right sides, a separate strap attachment with at least one strap joined thereto at two points, said strap attachment further projecting at least one strap through slots on each side of said fastening plate through a support webbing for said fastening plate, said straps further joined to a means for anchoring to said straps a body fastening strap.

8. A back support device as defined in claim 1 and wherein said fastening plate follows the sagittal course of a lumbar vertebral column up to the coccyx and tappers at the lower end and is bent thereafter towardly said rib plate.

9. A back support bandage device as defined in claim 8 and wherein said tapered lower end of said fastening plate is curved upwardly towards the side of said rib plate.

10. A back support device as defined in claim 1 and wherein said rib plate has, in its central region, over the entire length of said ribs, a cutout portion, a vertical edge region with at least one rib thicker than said remaining ribs, and a combination of a cutout portion and a thicker rib.

* * * * *